United States Patent
Jacobs et al.

(10) Patent No.: US 6,232,773 B1
(45) Date of Patent: May 15, 2001

(54) CONSISTENT DRAG FLOATING BACKING BAR SYSTEM FOR PIPELINE PIGS AND METHOD FOR USING THE SAME

(75) Inventors: Scott K. Jacobs; Robert S. Evenson; Donald M. Macaulay, all of Calgary (CA)

(73) Assignee: BJ Services Company, Houston, TX (US)

(*) Notice: Subject to any disclaimer, the term of this patent is extended or adjusted under 35 U.S.C. 154(b) by 0 days.

(21) Appl. No.: 09/148,977

(22) Filed: Sep. 5, 1998

(51) Int. Cl.[7] ............................. G01N 27/72; G01N 27/82
(52) U.S. Cl. ............................. 324/220; 324/242
(58) Field of Search .................................. 324/220, 219, 324/221, 226, 228, 236, 237, 238, 242–243, 262; 104/138.2

(56) References Cited

U.S. PATENT DOCUMENTS

| | | | |
|---|---|---|---|
| 4,675,604 | * | 6/1987 | Moyer et al. ........................... 324/240 |
| 4,797,613 | * | 1/1989 | Wentzell ................................ 324/220 |
| 5,313,838 | * | 5/1994 | Gondard et al. ....................... 324/226 |
| 5,359,939 |   | 11/1994 | Walt ................................... 104/138.2 |
| 5,537,035 | * | 7/1996 | Fowler et al. ......................... 324/220 |
| 5,565,633 | * | 10/1996 | Wernicke .............................. 73/865.8 |
| 5,623,203 | * | 4/1997 | Hosohara et al. ..................... 324/220 |
| 5,864,232 | * | 1/1999 | Laursen ................................ 324/242 |

OTHER PUBLICATIONS

Robert S. Evenson, M.Sc., P. Eng and Scott K. Jacobs, B.Sc. Mechanical Engineering, *Mechanical Development of a NPS 26 Speed Controlled Pipeline Corrosion Measurement Tool*, International Pipeline Conference (vol. 1), 1998, at 351–355.

* cited by examiner

*Primary Examiner*—Jay Patidar
(74) *Attorney, Agent, or Firm*—Howrey Simon; Arnold & White, LLP

(57) ABSTRACT

A pipeline pigging device including a vehicle movable within a pipeline having shape deformations is provided. The vehicle provides a predetermined axial length and outside diameter to define an exterior surface. A plurality of floating backing bar systems are circumferentially mounted on the external surface along the axial length of the vehicle. The floating backing bar system radially extends by a compression force away from the vehicle to contact and introduce a consistent force on the inside pipeline wall as the device moves through the pipeline.

19 Claims, 10 Drawing Sheets

CONSISTENT DRAG FLOATING BACKING BAR SYSTEM FOR PIPELINE PIGS AND METHOD FOR USING THE SAME

FIELD OF THE INVENTION

This invention relates in general to a floating backing bar system for a pipeline pigging device, and more particularly to a process of using device for creating more consistent and stable drag as well as lowering stress and wear being produced in the suspension system and tool superstructure of an in-line pipe tool during longitudinal travel of the tool through a pipeline.

BACKGROUND OF THE INVENTION

Pipeline pig tools are devices that are used in a variety of applications, including inspection, cleaning, coating, and cutting of the pipeline. It is well known to perform in-line inspections of a pipe by magnetic flux leakage ("MFL") technology. With this inspection practice, an in-line pipe inspection tool is propelled through the pipeline by the product flowing therein, which for example may be oil or gas. The vehicle is propelled along the pipeline by the fluid or gas flow reacting with resilient cups that are mounted around the body of the vehicle and that are in contact with the pipe internal wall. The fluid or gas flow provides the necessary driving force to propel the vehicle by a differential pressure acting across the resilient cups.

As the tool passes through the pipeline, a strong magnetic field is induced into the pipe wall by an inspection tool attached to the vehicle. Defects in the form of discontinuities will cause redistribution of the magnetic flux around the defect. This results in some of the lines of magnetic flux leaking out into the surrounding medium. Though there is a constant magnetic flux leakage, a defect will cause a deviation in the flux leakage field which can be detected. The inspection tool may embody an electromagnet which is battery powered or permanent magnets to induce the magnetic flux field into the pipe wall.

Two sets of steel brushes mounted on the vehicle are commonly used in conjunction with the magnet to constitute the magnetic north and south poles of the magnetic flux field. It is necessary to maintain constant contact between the two sets of brushes and the internal surface of the pipe to ensure an uninterrupted magnetic flux field within the pipe wall. A plurality of transducers mounted on the vehicle are used to detect deviations in the magnetic flux leakage field indicating a defect in the pipe wall. The two sets of steel brushes employed with the magnetizer also act to support the inspection tool during its travel through the pipe.

In order to obtain useful and reliable data, slow inspection tools are used that normally travels at speeds less than four meters per second (m/s). As most gas pipelines operate at velocities far in excess of this speed, reducing pipeline flow velocities to provide an optimum MFL measurement environment is one accepted standard for MFL corrosion measurement. However, even at these lower speeds variations in the differential pressure can lead to fluctuations in vehicle speeds, with consequently high and unacceptable accelerations and declarations, resulting in poor MFL data acquisition. Usually the differential variations are caused by shape deformations in the pipeline wall, such as changes in wall friction characteristics, welds, junctions, bends and/or changes in the pipeline wall thickness.

One method of accounting for these changes in differential pressure is to utilize a speed control which features a bypass valve to allow gas within the pipeline to bypass the resilient cups and hence control the differential pressure across the cups. The use of a bypass system has not proved completely satisfactory.

Low MFL tool measurement speed and lack of active speed control bypass capabilities generally resulted in a plethora of economic and operational problems for high pressure gas pipeline operators. Reducing gas or fluid velocities to a fraction of normal throughput velocity was not uncommon and generally resulted in an operational pipeline outage. Economic impact due to lost throughput and operational problems associated with attempting to reduce product flow caused major concerns. Other active speed controlled tools for pipeline have been previously conceived, but it is believed that practical attempts at operating and acquiring MFL data at approximately low tool velocities, without operational impact, have been unsuccessful.

Another concern in MFL inspection tools is excessive wear and deformation of the steel brushes utilized in creating and maintaining the magnetic flux field. After extended use of the inspection tool, these steel brushes tend to wear and deform as a result of the combination of the weight of the inspection tool being supported, the weight of the fluid in the pipe above the inspection tool and contact with the interior surface of the pipe. Changes in wall friction characteristics, welds, junctions, bends and/or changes in the pipeline wall thickness also tend to increase the wear and deformation of the steel brushes. This results in misposition of the inspection tool during travel through the pipe and discontinuous contact between the steel brushes and the interior pipe wall surface. This adversely affects the desired uninterrupted magnetic flux field in the pipe wall necessary for effective defect detection. This condition is further exacerbated when pipe diameters vary.

With these applications the brushes are required to extend sufficiently to support the tool with increased diameter pipe and then compress when inspecting smaller diameter pipe. During extension of the brushes, there must be sufficient force exerted by the brushes against the pipe wall to provide the required contact to ensure an uninterrupted magnetic flux field within the pipe wall. Compression results in excessive wear and deformation of the brushes for in-line inspection tools. Therefore there is a need for a mechanical support device that ensured the best possible consistent sensor/wall engagement to optimize detection of magnetic flux leakage, without operational impact.

Similar problems are encountered in the other fields of pipeline pigging tools where speed control and/or support of the pipeline pig is a necessary feature and/or where excessive wear or deformation of tools contacting the interior surface of the pipeline is a problem. For example, pipeline cleaning pigs commonly comprise a body that support one or more cleaning, scraping or crushing tools for cleaning the interior of the pipeline. Differential variations in the pipeline caused by changes in wall friction characteristics, welds, junctions, bends and/or changes in the pipeline wall thickness often cause excessive wear, deformation or breakage of the tools. If the cleaning pig suffers a catastrophic failure while inside the pipeline, the metal fragments from the tools may become lodged in the wall of the pipeline or in valves or pipeline junctions, or they may damage downstream equipment such as pumps or sensors.

It would be desirable to design a suspension system for use with an in-line pipeline pigging tool that would be operable in average high pressure pipeline systems without providing an operational impact on the pipeline system or product throughput. Such an invention would minimize velocity variations due to changing line conditions by introducing drag into the system that is consistent, tunable and relatively constant through varying wall thickness, be modular in design for ease of serviceability and interchangeability, and durable to withstand potential speed excursions, while minimizing loading due to pipeline constraints commonly found in the industry.

SUMMARY OF THE INVENTION

In a first embodiment, the present invention provides a pipeline pigging device having a vehicle movable within a pipeline having shape deformations. The vehicle provides a predetermined axial length and outside diameter to define an exterior surface. A plurality of floating backing bar systems are circumferentially mounted on the external surface along the axial length. The systems radially extend by a compression force away from the vehicle to contact and introduce a consistent force on the inside pipeline wall as the device moves through the pipeline.

In still another embodiment, a method is provided for the inspection of a pipeline having shape deformations. In particular, the method includes: positioning an inspection vehicle having an inspection device and a floating backing bar system, the floating backing bar system having frictional elements mounted on the external surface of the backing bar system adjacent the inside wall of the pipeline; passing a fluid through the pipeline to cause the inspection vehicle to move their along; and causing the frictional elements on the floating backing bar systems of the inspection vehicle to contact the inner wall of the pipeline with a consistent force.

BRIEF DESCRIPTION OF THE DRAWINGS

Other aspect and advantages of the invention will become apparent upon reading the following detailed description and upon reference to the drawings.

FIG. 2-B illustrates an exploded bottom-end isometric view of the mounting structure illustrated in FIG. 2-A.

FIG. 2-C illustrates an isometric view of the force suspension system in accordance with an alternative embodiment of the invention.

Figure 1:
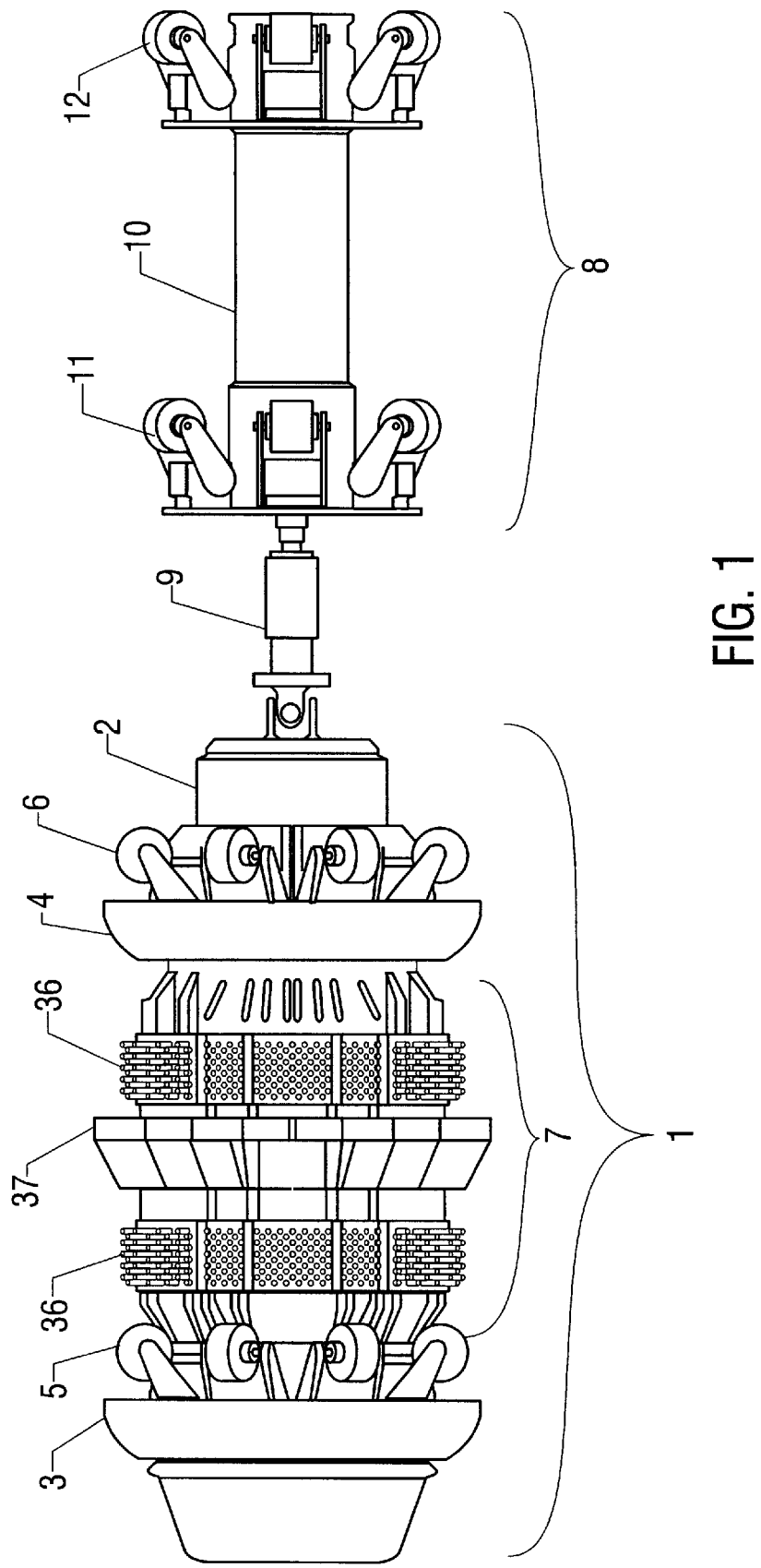
FIG. 1 illustrates a isometric view of a pipeline pigging device in accordance with a first embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be routine undertaking for those of ordinary skill in the art having the benefit of this disclosure.

Referring now to the drawings, FIG. 1 illustrates an isometric view of one embodiment of the present invention described in relation to a speed controlled MFL ("magnetic flux leakage") pipeline corrosion inspection device. This device consists of two vehicles which are linked together by a flexible coupling means. The conventional tractor vehicle 1 comprises a main tubular body 2 having flexible low friction driving cups 3 and 4 and support wheel units 5 and 6 attached thereto. The inventive floating backing bar system 7, in accordance with a first embodiment, mounts between driving cups 3 and 4 on an exterior surface of main tubular body 2. Tractor vehicle 1 tows conventional support vehicle 8 with a flexible coupling element 9. The towed vehicle comprises a main tubular body 10 having wheeled suspension units 11 and 12 that accurately record distance, a data acquisition/storage system (not shown) to record store sensor output, and batteries to provide power (not shown).

Figure 2A:
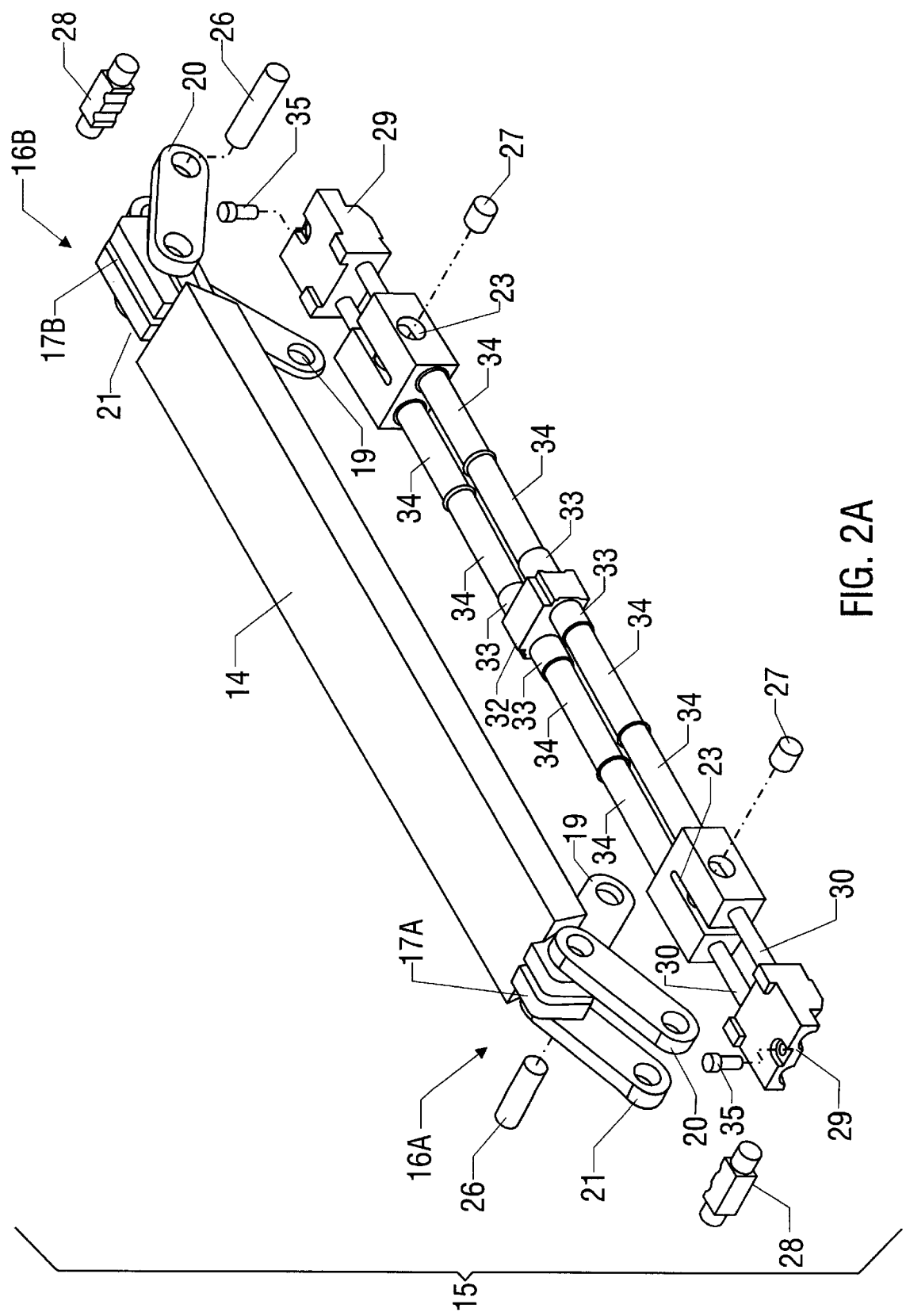
FIG. 2-A illustrates an exploded isometric view of a single backing bar mechanism as shown in FIG. 1.
Figure 2B:
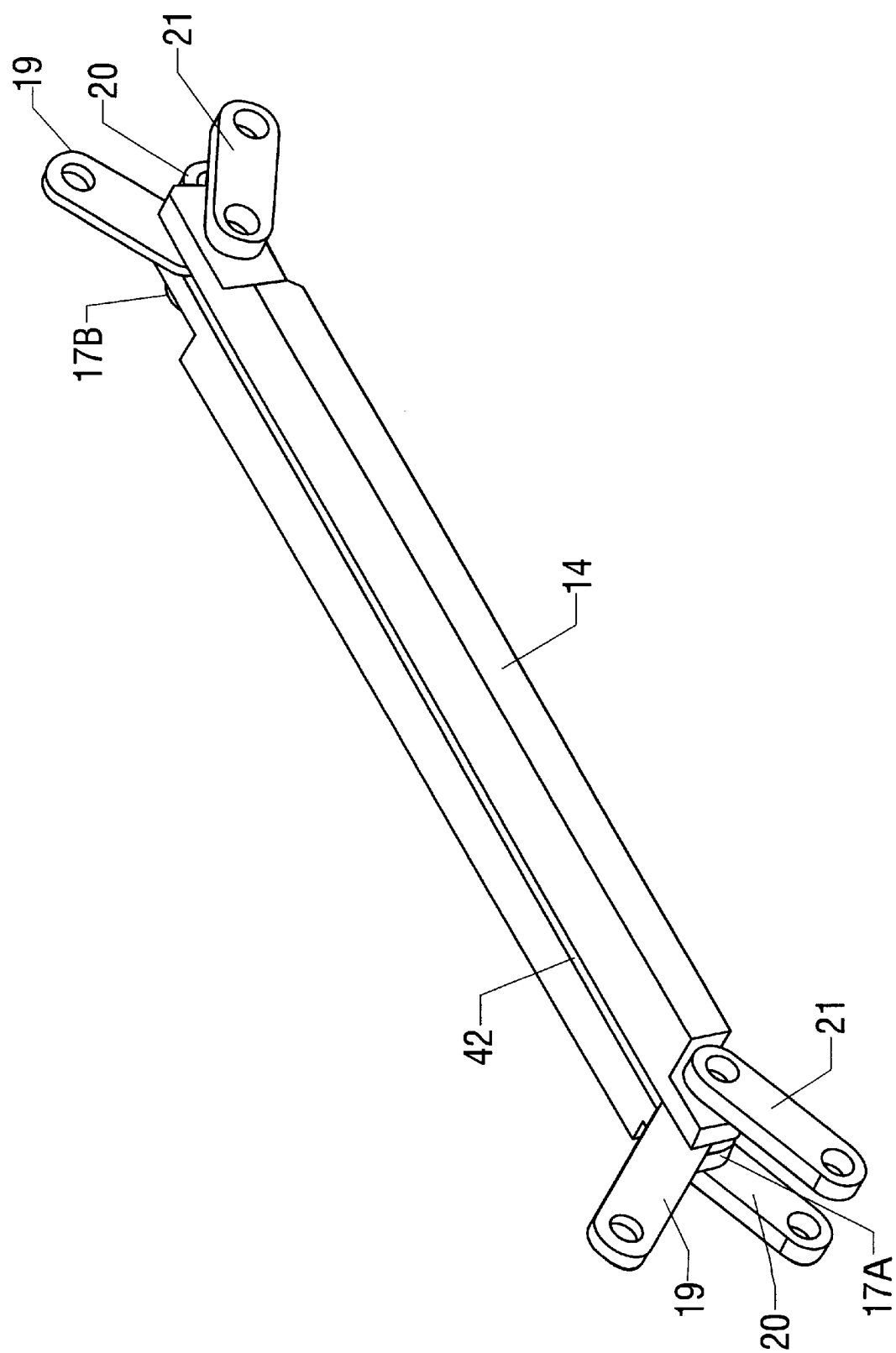
Figure 2C:
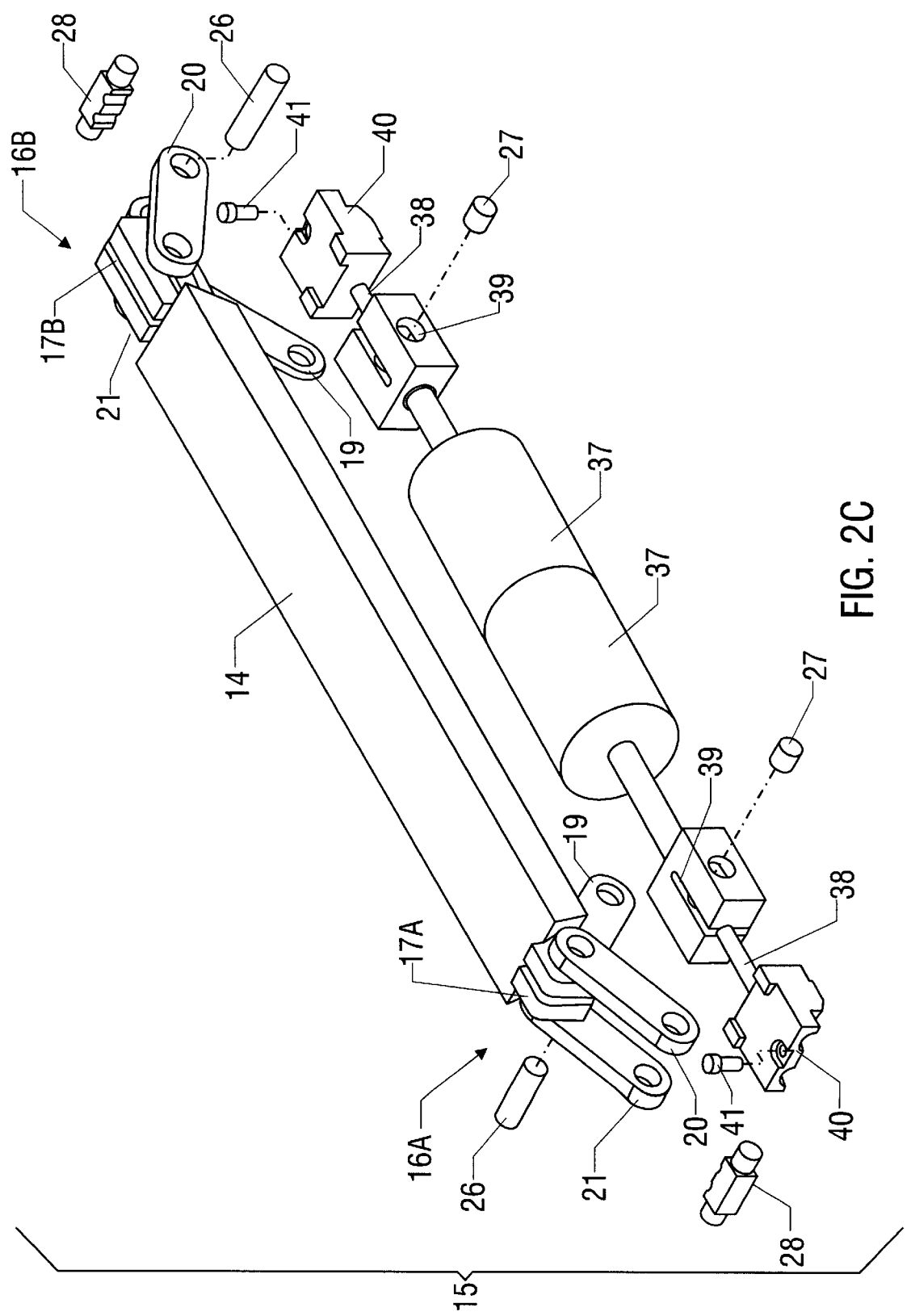

FIG. 2-A shows an exploded isometric view of a single backing bar mechanism of the floating backing bar system 7 as illustrated on tractor vehicle 1 of FIG. 1. In general, backing bar system 7 comprises a mounting structure 14 attached and to force suspension system 15 by two linkage assemblies 16A and 16B.

Each linkage assembly 16A and 16B consists of three pivot arms, 19, 20 and 21. Pivot arm 19 mounts between linkage joints 17A and 17B of mounting structure 14 and slideable mount 23 of force suspension system 15 by securing pivot pins 26 and 27, respectively. The mounting structure 14 has a groove 42 (See FIG. 2-B) cut into the underside surface that runs along the longitudinal axis of the mounting structure. The groove length and central orientation allows pivot arms 19 a range of travel underneath the mounting structure 14 to attain a position nearly parallel to the mounting structure 14 when force suspension system 15 is compressed and linkage assemblies 16A and 16B are completely collapsed underneath the mounting structure 14. (See FIG. 5).

Pivot arms 20 and 21 mount at one end to linkage joints 17A and 17B of mounting structure 14 and at the other end to pivot mounts 24 (See FIGS. 3–5) of main tubular body 2 by securing pivot pins 26 and 28, respectively. It should be appreciated by persons of ordinary skill in the relevant arts that linkage assemblies 16A and 16B can be disassembled and replaced with new pivot arms (not shown) having a varied length to change the suspension and linkage geometry. Consequently, the pivot arms can be used to dictate the travel distance and force obtainable for the backing bar mechanism 7 of FIG. 1, and account for changes in wall friction characteristics, welds, junctions, bends and/or changes in the pipeline wall thickness, as well as use of the vehicle in pipes of varying diameter.

Force suspension system 15 consists of two sets of two parallel spring rods 30 having an equal length. Each spring rod set 30 connect between rod attachment plates 29 and a centrally located fixed barrier 32. Four spacers 33 and eight springs of equal tension 34 mount on rods 30 in equal numbers and on either side of fixed barrier 32 (two spacers and four springs per rod, with one spacer and two springs on each side of the fixed barrier). Spacers 33 and springs 34 are positioned proximal and distal, respectively, to the fixed barrier 32. Additionally, two slideable mounts 23 are located and mounted on rods 30 between rod attachment plate 29 and springs 34. The force suspension system 15 connects to the exterior surface of the main tubular body 2 (see FIG. 1) at the rod attachment plates 29 by securing bolts 35. It should be appreciated by persons of ordinary skill in the relevant art that the force suspension system can be disassembled and replaced with new springs and spacers (not shown) to adjust the spring rate. Consequently, by changing the springs 34 to a different tension and/or by adding or removing spacers 33 to change the preload (the initial compression), the user can dictate the speed and force obtainable for the backing bar mechanism 7 of FIG. 1.

An alternative embodiment of the force suspension system 15 consists of at least two conventional adjustable compression rate piston and cylinder assemblies 37 mounted end to end, two slide-rods 38, two slideable mounts 39, and two slide-rod attachment plates 40. (See FIG. 2-C ). The force suspension system 15 connects to the exterior of the main tubular body 2 at the slide-rod attachment plates 39 by securing bolts 41. It should be appreciated by persons of ordinary skill in the relevant art that the force suspension system can also be disassembled and replaced with new adjustable compression rate pistons and cylinder assemblies (not shown) to adjust the compression rate.

Figure 3:
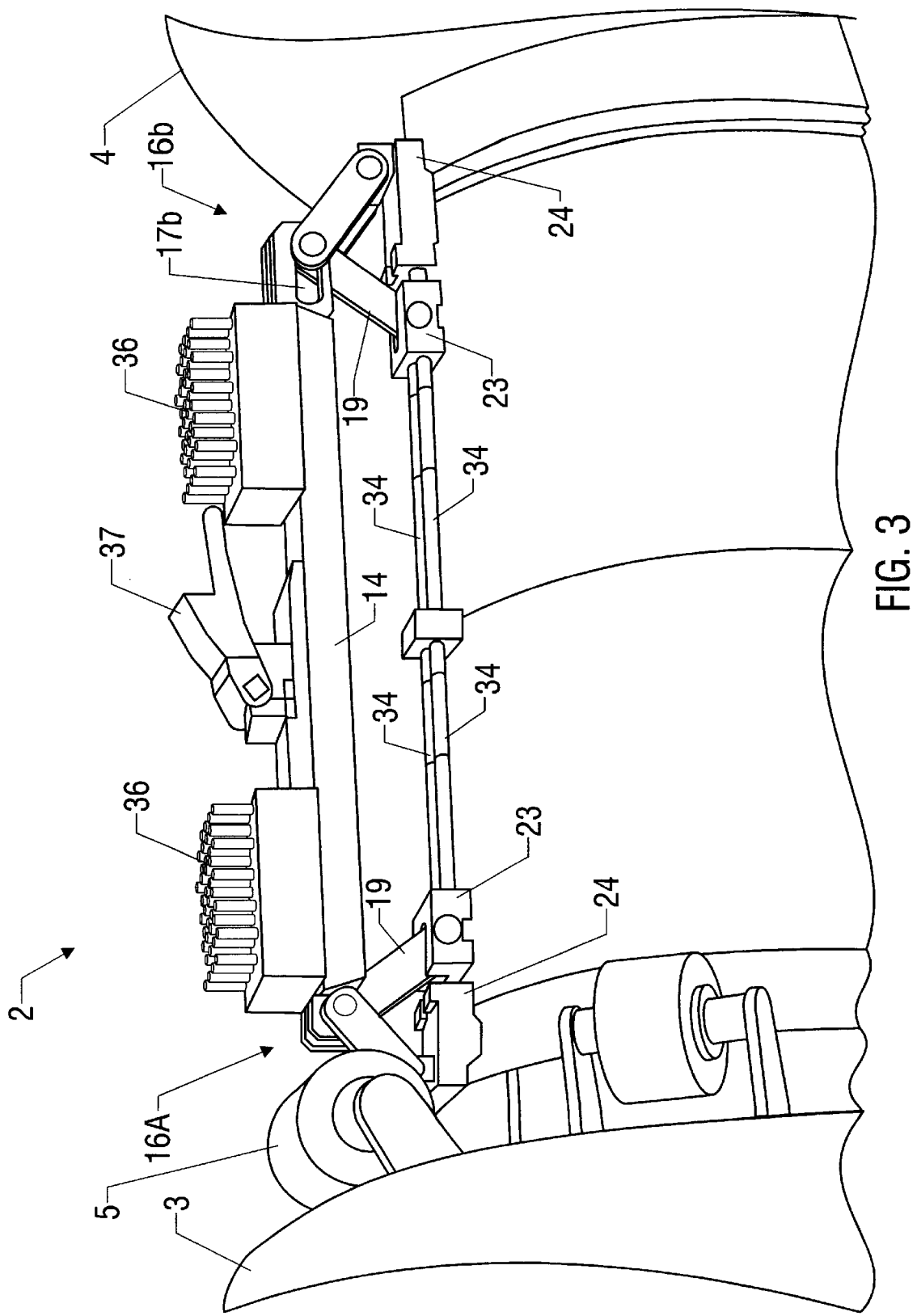
FIGS. 3–5 illustrate an isometric view of the pipeline pigging device of FIG. 1 during operation.
Figure 4:
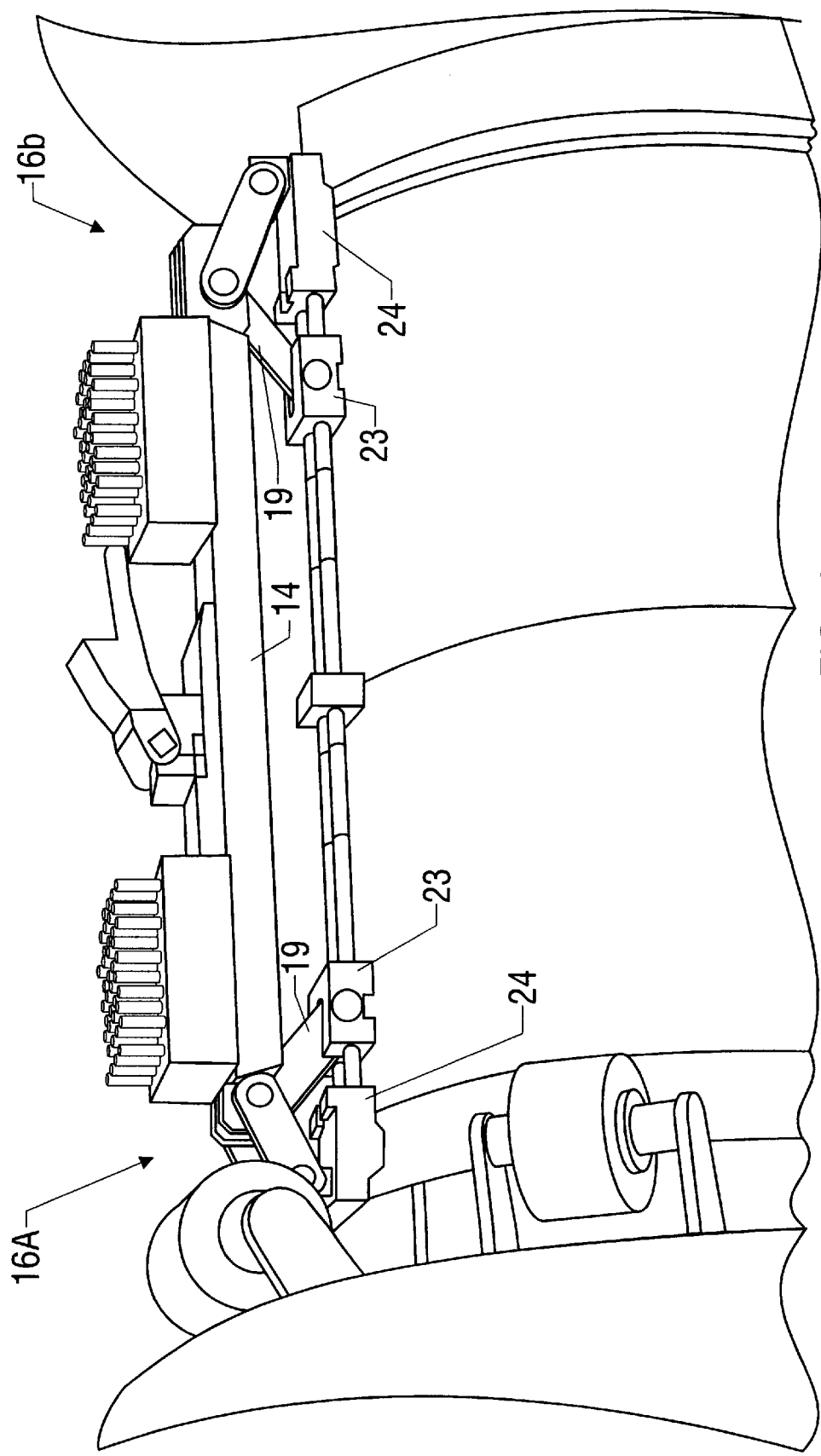
Figure 5:
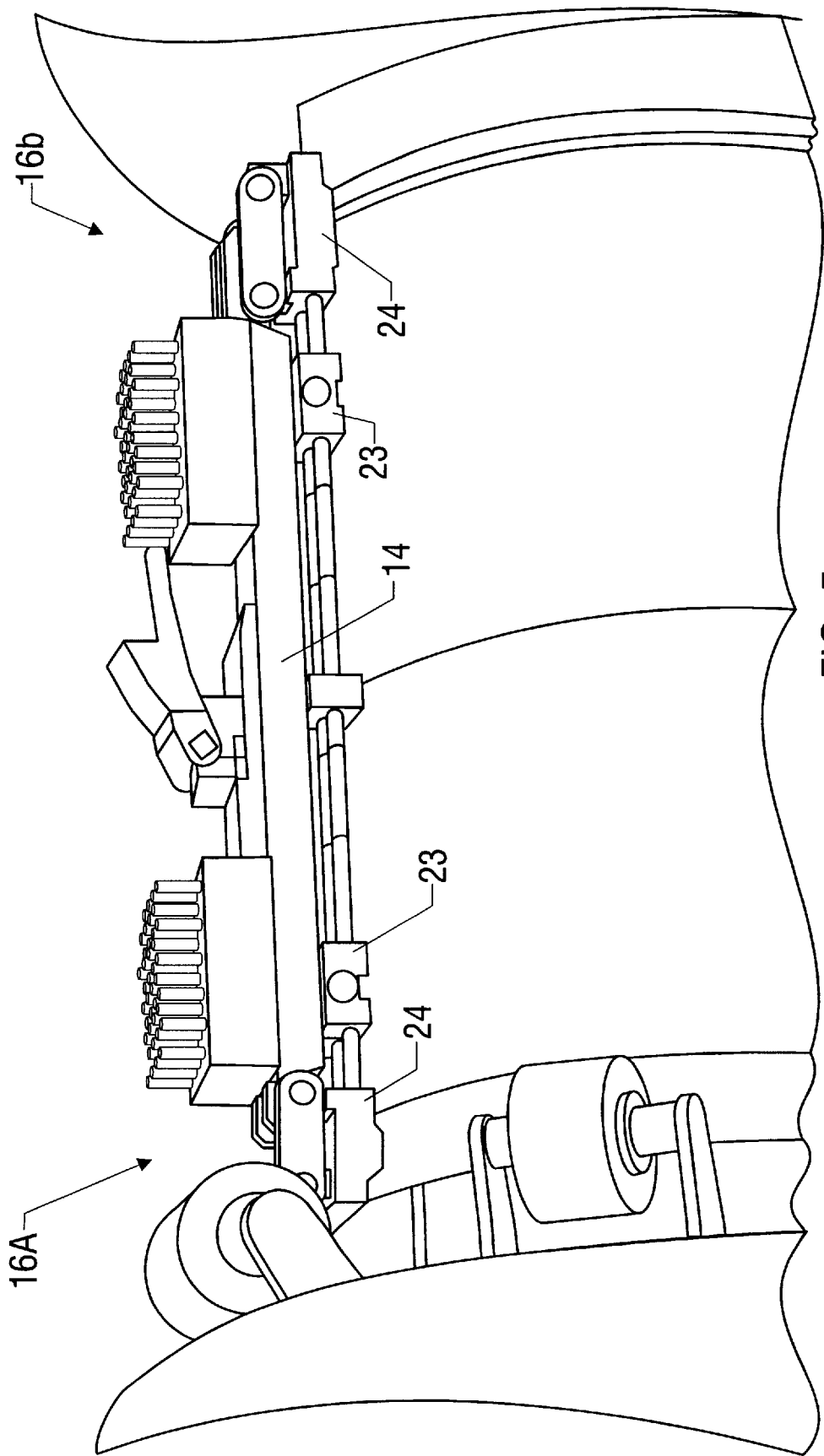

The floating backing bar systems 7 described above can be used to supplement any speed control system to provide a more consistent and stable drag. FIGS. 3–5 show a magnified isometric view of the floating backing bar mechanism 7 for the speed control device in FIG. 1. Brushes 36 and a pivoting MFL sensor 37 mount on the external surface of mounting structure 14.

As the pipeline corrosion inspection device is inserted in a pipeline (not shown) springs 34 of force suspension system 15 introduce an axial force that is translated through the linkage assemblies 16A and 16B to backing bar mounting structure 14. This axial force causes the backing bar mounting structure 14 to move in an outwardly radial direction until the external surface of brushes 36 reach the pipeline wall imparting a normal force to the pipeline wall through the brushes 36. (See FIG. 3). The normal force introduced at the pipeline wall results in an axial friction force preventing the tool from moving until the friction force resulting from the coefficient of friction is exceeded by an opposing lateral force. This axial friction force, $F_f$,(parallel to the pipe wall) is a function of the normal force, $F_N$,(perpendicular to the pipe wall) and the coefficient of friction, $\mu$, between the brushes and the pipe wall. The relationship between the frictional and normal force is given by:

$$F_f = \mu F_N$$

As discussed above, the resulting force vs. displacement curve of the backing bar system can be changed, adjusted or fine tuned to provide virtually constant drag forces over specific displacement ranges by adjusting the spring rate and the geometry of the suspension and linkage.

As the device moves through the pipeline it may encounter changes in the inside pipeline conformation caused by narrowing of the pipeline, pipeline bends and/or obstructions and other constrictions. As the device encounters these changes the floating backing bar system adjusts by compressing inwards. (See FIGS. 4 and 5). Backing bar mounting structure 14 movement is allowed through the rotation of the outer linkages assemblies 16A and 16B about the linkage joints 17A and 17B. A slot is present at the rear linkage joint 17B to accommodate the axial pin translation due to the linkage assembly rotation (See FIG. 4 and 5); thereby all of the frictional forces acting on the mounting structure 14 are transferred to the backing bar mechanism through linkage joint 17A only. Compression of the backing bar mounting structure 14 results in rotation of the pivot arms 20 and 21 about the linkage joints 17A and 17B. This rotation results in a change in the linkage joint's 17B axial location which translates into a movement of the two slideable mounts 23 and hence a change in the force exerted on the slideable mounts 23 by the springs 34. The spring force is exerted on the system in an axial direction and is translated to a normal force through the linkage assemblies 16A and 16B. This relationship is given by:

$$F_N = F_S(\tan(\alpha) + \tan(\beta))$$

Figure 10:
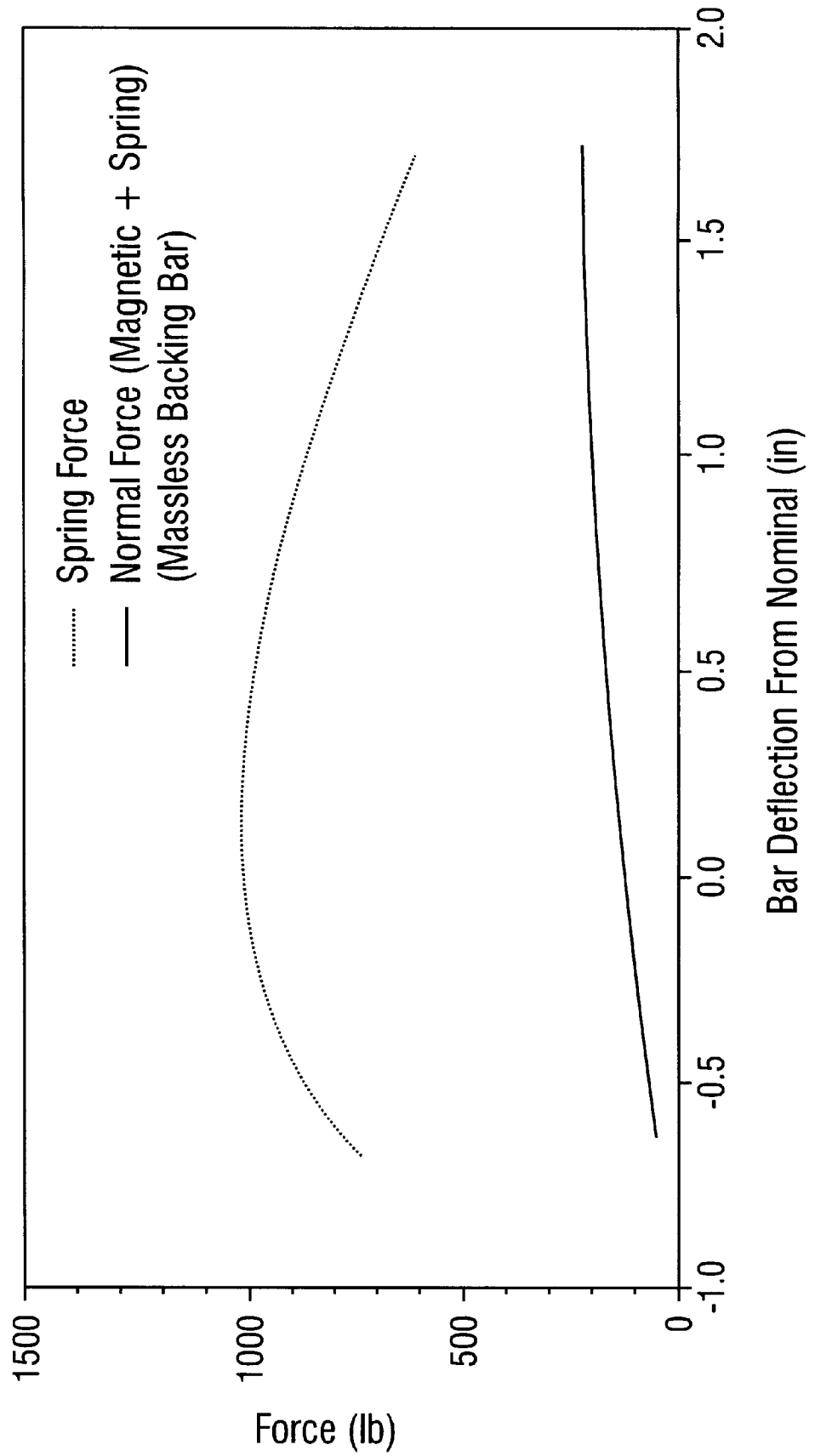
FIG. 10 illustrates a graph reciting spring and normal force versus backing bar deflection during operation of the apparatus in FIG. 1.

The equation expresses the normal load applied at each end of the mounting structure 14 bar due to the total spring force applied at each end. For a constant spring force the normal load will decrease as the backing bar mounting structure 14 is depressed radially inward. The spring force, or course, does not stay constant, but rather increases as the mounting structure 14 is depressed radially inward. (See FIG. 10) Therefore the length (absolute and relative) of the pivot arms 19, 20 and 21, their initial angles with respect to the mounting structure 14, the spring rate of the springs 34 and their initial compression (or preload) and the allowable backing bar mechanism travel all effect the resulting normal force relative to backing bar position relationship.

Utilizing conventional backing bar suspension would result in an increasing normal force with inward bar deflection. Increases in normal force introduced at the pipeline wall result in an increase in the axial friction force, which results in a change in the drag of the tool as is travels through the pipe. Since normal forces in the nominal tool position are designed to be high to optimize drag, brush loading would become unmanageable when a bar is fully depressed using conventional suspension. Further, constant drag through varying wall thickness would not be obtained nor brush wear minimized. These problems would be further exaggerated in attempting to navigate three dimensional bends, large dents and pipe ovality where the tool is forced to comply to pipe geometry.

A unique feature of the present invention is that normal forces imparted through the backing bar mechanism reduce as the assembly is compressed inwards; this is opposite of conventional suspension utilized on other known applications of backing bars on pipeline pigging devices. This results in a more consistent and stable drag as well as lowering stresses being produced in the backing bar and the tool superstructure as the tool complies to pipeline bends and constrictions.

Although the invention is described and illustrated based on an in-line inspection tool, other applications are available and would be appreciated by persons of ordinary skill in the relevant art. For example, the present invention as described above can be used for cleaning. When deposits develop on the interior walls of the pipeline, abrasive materials, scraping tools or cutting tools can be mounted on the external mounting surface of the backing bar mechanisms.

While the preferred embodiment of the invention has been described and alternative configurations have been suggested, it should be understood that other embodiments may be devised and modifications can be made thereto without departing from the spirit of the invention and the scope of the appended claims.

MATERIALS

Typically, most of the rigid elements will be made of metal commonly used in the pigging industry, e.g. aluminum or steel. If the backing bar mechanism is to be utilized in a MFL inspection tool, it is recommend that the backing bar mechanism mounting plate be made of low carbon steel to accommodate magnetic flux requirements. Additional reinforcing materials used for cleaning, scraping or abrading may include metal wires, cord, nylon, or kevlar. It is recommend that such additional reinforcing materials not be soluble to any substantial degree in the oil or gas or anti-corrosive agents used in the pipeline. Other suitable materials are known to those skilled in the art.

The following example further illustrates the practice of this invention.

Figure 6:
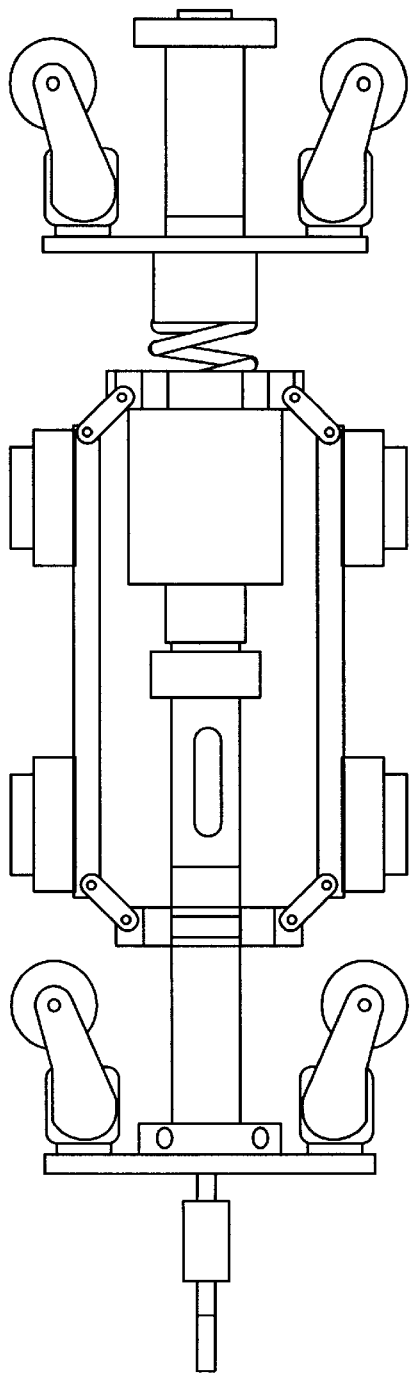
FIG. 6 illustrates a cut away view of the pipeline pigging device built for testing the floating backing bar system in accordance with FIG. 1.

An apparatus designed and built for testing the floating backing bar system is shown in FIG. 6. Several types and configurations of brushes and variations in backing bar suspension were tested. The tool was drawn through an experimental pullrig under varying velocity and loading conditions in both dry and oily pipe. To determine the coefficient of friction, sensors were affixed to resolve normal force and resultant friction force (drag) components between the brushes and pipe wall. Parallel testing was done to determine the magnetic characteristics of different brush types and configurations.

Figure 7:
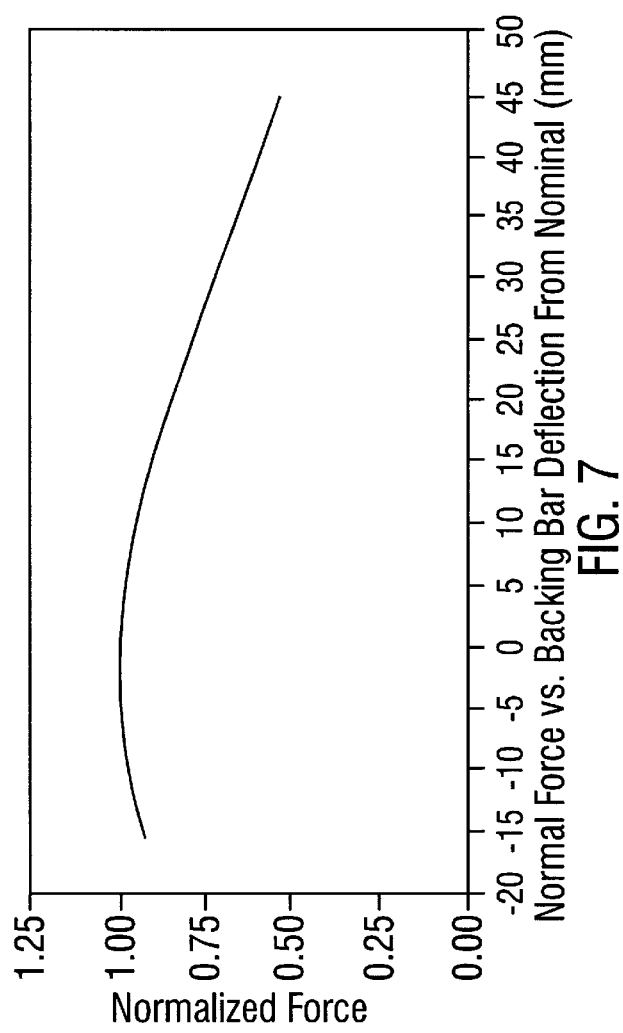
FIG. 7 illustrates a graph reciting normal force versus backing bar system deflection during operation of the apparatus in FIG. 6.

As can be seen in FIG. 7, in tests of the floating backing bar system on a MFL inspection tool that would operate in a average NPS 36 high pressure natural gas pipeline, a nearly constant normal force was maintained by the brushes against the inside wall of the pipeline. Deflections within twelve (12) mm of the nominal position, exhibit normal force deviations less than eight percent (8%). Moreover, normal brush force actually decreases as the bar deflects. This effect was enhanced by using a low spring constant with a high initial compression. The system is also tunable and can be adapted to varying line conditions and run lengths simply by changing the springs and/or their preload.

Figure 8:
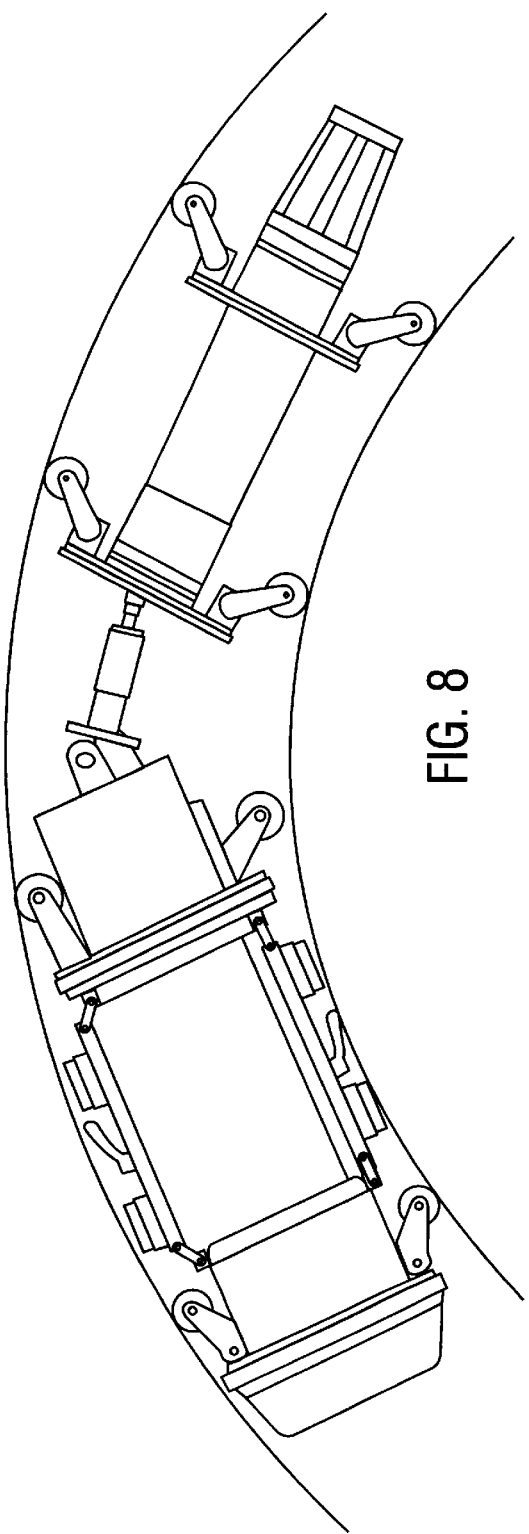
FIGS. 8 and 9 illustrate a cut away view of the inventive pipeline pigging device during operation using the apparatus in FIG. 6.
Figure 9:
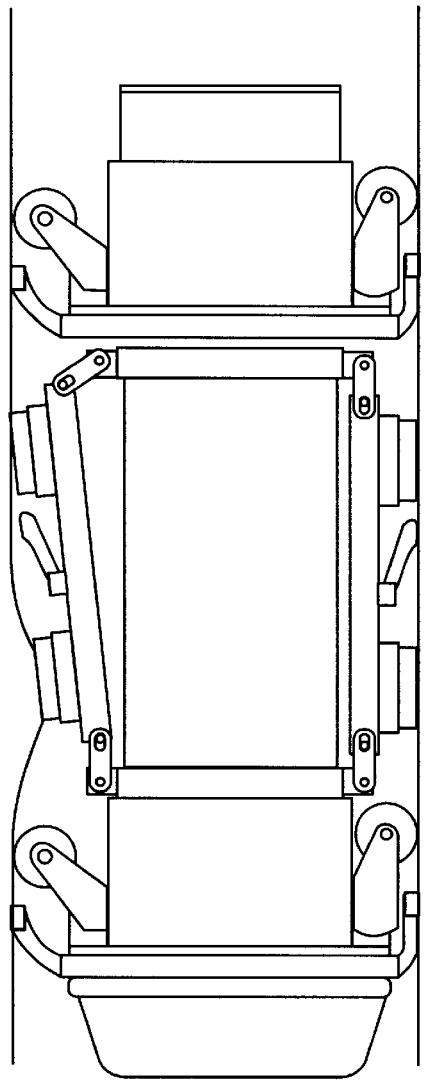

The tool's ability to negotiate a two-point-eight degree (2.8 D) bend and a ten percent (10%) dent is shown in FIGS. 8 and 9 respectively.

In summary, the present invention as described above provides various embodiments for a novel floating backing bar system that can be used with a pipeline pigging device. In particular, this system can enhance active speed control by providing more consistent and stable drag and provide support for mounting inspection tools. If the mounting tools are brushes, the inventive system will minimize brush wear of an in-line MFL pipeline inspection tool. Lastly, all these benefits are provided even in the presence of differential variations that are caused by changes in wall friction characteristics, such as welds, junctions, bends and/or changes in the pipeline wall thickness, so that it runs at consistent, optimum measurement velocities substantially lower than line velocity.

What is claimed is:

1. A pipeline pigging device comprising:
   a vehicle movable within a pipeline having shape deformations, said vehicle providing a predetermined axial length and outside diameter to define an exterior surface; and
   a plurality of floating backing bar systems circumferentially mounted on said exterior surface, wherein each of said floating backing bar systems comprises:
      a force suspension system attached to said exterior surface and a mounting structure attached to said force suspension system;
   wherein said floating backing bar systems radially extend by a compression force away from said vehicle to contact and introduce a consistent force on the inside pipeline wall as said device moves through said pipeline; and
   wherein said suspension system reduces said compression force as said mounting structure collapses on said exterior surface.

2. The device of claim 1, wherein each one of said plurality of floating backing bar systems further includes:
   a first and a second linkage assembly coupled between respective first and second adjacent end portions of said mounting structure and said force suspension system.

3. The device of claim 2, wherein said force suspension system further includes:
   a first and a second attachment plate connected to said exterior surface adjacent the distal ends of said mounting structure; and
   a force mechanism couples between said first and second attachment plates.

4. The device of claim 3, wherein each said linkage assembly further includes at least two arms pivotally coupled together at one end to said mounting structure and at the other ends between said force mechanism and said attachment plate.

5. The device of claim 3, wherein said force mechanism introduces said compression force to move said mounting structure up and down in a radial direction from the exterior surface to define a predetermined suspension travel.

6. The device of claim 5, wherein said predetermined suspension travel of said floating backing bar system is defined by the outside surface of the mounting structure reaching the inside pipeline wall to impart a normal force to the wall resulting in an axial friction force preventing said device from moving until the friction force resulting from the coefficient of friction is exceeded.

7. The device of claim 4, wherein said force mechanism further comprises:
   at least two springs;
   at least one rod fixably mounted through said springs and between said attachment plates;
   a fixed barrier located at the midpoint of said rod; and
   a first and a second slideable mount attached to said rod and respectively coupled to said first and second linkage assemblies, said springs being coupled between said fixed barrier and said first and second slideable mount.

8. The device of claim 4, wherein the force mechanism further comprises:
   at least one spring;
   at least one rod fixably mounted through said spring and between said attachment plates;
   and a first and a second slideable mount attached to said rod and respectively coupled to said first and second linkage assemblies, said spring being coupled between said first and second slidable mount.

9. The device of claim 8, wherein said force mechanism further includes mounting spacers positioned between said spring and said slideable mount to change said compression force.

10. The device of claim 4, wherein the force mechanism further includes:
   at least two pistons coupled to said first and second linkage assembly, respectively; and
   at least two adjustable compression rate cylinder assemblies mounted end to end on said exterior surface such that the longitudinal axis of the cylinders run parallel with the longitudinal axis of said pipeline, each said piston moves in and out of the respective cylinder to radially move said mounting structure.

11. The device of claim 2, further including at least one frictional element mounted on an outside surface of said mounting structure adjacent said inside pipeline wall.

12. The device of claim 11, wherein said at least one frictional element is selected from the group comprising brushes, braking pads, cleaning adhesive, and fluid dispensers.

13. The device of claim 1, wherein inwardly radial deflections of the mounting structure caused by inside pipeline wall deformations results in a decrease in the imparted normal force of said consistent force, to the inside pipeline wall to provide a consistent drag on said inside pipeline wall deformations while the device moves through said pipeline.

14. The device of claim 1, wherein said vehicle is a MFL pipeline corrosion inspection device.

15. The device of claim 1 wherein the attachment between the mounting structure and the force suspension system is accomplished by at least one linkage assembly.

16. The device of claim 15 wherein the at least one linkage assembly comprises a plurality of rotatable pivot arms and a slide mount attached to a first of said plurality of rotatable pivot arms;
   wherein compression of the mounting structure results in rotation of at least a second of said plurality of pivot arms about said at least one linkage assembly to change the axial position of said at least one linkage assembly and consequently change a force exerted on said slidable mount by at least one spring, wherein said force exerted on said slidable mount is translated to said compression force through said at least one linkage assembly, said compression force decreasing upon compression of the mounting structure according to the formula:

$$F_{compression} = F_{spring}(\tan \alpha)$$

where $\alpha$ is the angle between said slidable mount and said first of said plurality of rotatable pivot arms.

17. A pipeline pigging device comprising:
   a vehicle movable within a pipeline having shape deformations, said vehicle providing a predetermined length and outside diameter to define an exterior surface;
   a plurality of consistent drag systems circumferentially mounted on said exterior surface along an axial length of said pipeline, each of said systems comprising:
      a mounting structure;
      a first and a second attachment plate connected to said exterior surface adjacent the distal ends of said mounting structure;
      a force mechanism coupled between said first and second attachment plates; and
      first and second control linkages pivotally coupled between respective first and second distal ends of said mounting structure, attachment plate, and force mechanism.

18. The device of claim 17, wherein said systems radially extend by said force mechanism away from said exterior surface to contact and introduce a consistent force on the inside pipeline wall as said device moves through said pipeline deformations.

19. A method for inspecting a pipeline with shape deformations comprising:
   positioning an inspection vehicle having an inspection device and a floating backing bar system within the pipeline, said floating backing bar system comprising:
      a force suspension system attached to said vehicle;
      a mounting structure attached to the force suspension system by at least one linkage assembly, and
      frictional elements arranged about the mounting structure adjacent the inside wall of said pipeline;
   passing a fluid through said pipeline to move said inspection vehicle through the pipeline; and
   causing said frictional elements on said floating backing bar system of said inspection vehicle to contact the inner wall of the pipeline with a consistent force.

* * * * *